US010299920B2

(12) United States Patent
Weber et al.

(10) Patent No.: US 10,299,920 B2
(45) Date of Patent: May 28, 2019

(54) EXPANDABLE ANNULUS SEALING RING FOR STENTED MINIMALLY INVASIVE HEART VALVE PROSTHESES

(71) Applicant: UNIVERSITAT ZURICH, Zurich (CH)

(72) Inventors: Benedikt Weber, Zurich (CH); Simon Philipp Hoerstrup, Zurich (CH)

(73) Assignee: UNIVERSITAT ZURICH, Zurich (CH)

( * ) Notice: Subject to any disclaimer, the term of this patent is extended or adjusted under 35 U.S.C. 154(b) by 0 days.

(21) Appl. No.: 15/512,103

(22) PCT Filed: Sep. 17, 2015

(86) PCT No.: PCT/EP2015/071383
§ 371 (c)(1),
(2) Date: Mar. 17, 2017

(87) PCT Pub. No.: WO2016/042108
PCT Pub. Date: Mar. 24, 2016

(65) Prior Publication Data
US 2017/0273786 A1 Sep. 28, 2017

(30) Foreign Application Priority Data
Sep. 18, 2014 (EP) .................................... 14185391

(51) Int. Cl.
*A61F 2/06* (2013.01)
*A61F 2/24* (2006.01)

(52) U.S. Cl.
CPC .......... *A61F 2/2418* (2013.01); *A61F 2/2433* (2013.01); *A61F 2210/0014* (2013.01); *A61F 2210/0061* (2013.01); *A61F 2210/0071* (2013.01); *A61F 2250/007* (2013.01); *A61F 2250/0036* (2013.01)

(58) Field of Classification Search
CPC ........ A61F 2/2409; A61F 2/2418; A61F 2/07; A61F 2210/0061; A61F 2250/0069
See application file for complete search history.

(56) References Cited

U.S. PATENT DOCUMENTS

| | | |
|---|---|---|
| 2006/0287717 A1 | 12/2006 | Rowe |
| 2011/0264206 A1 | 10/2011 | Tabor |
| 2014/0214157 A1* | 7/2014 | Bortlein ................ A61F 2/2418 623/2.11 |
| 2014/0243966 A1 | 8/2014 | Garde |

FOREIGN PATENT DOCUMENTS

| | | |
|---|---|---|
| WO | 2013/114214 | 8/2013 |
| WO | WO2013/114214 | 8/2013 |

* cited by examiner

*Primary Examiner* — Brian A Dukert
(74) *Attorney, Agent, or Firm* — JMB Davis Ben-David

(57) ABSTRACT

The invention relates to a medical implant, comprising an expandable structure (100) which is designed to be expanded from a crimped state into an expanded state, wherein the structure (100) forms a tubular scaffolding in the expanded state, and wherein the structure (100) comprises a plurality of first struts (101) arranged along a periphery of the structure in said expanded state. According to the invention, the first struts (101) each comprise a recess (O), wherein the medical implant (1) further comprises a sealing member (200) arranged in said recesses (O), wherein said sealing member (200) is formed annularly in said expanded state.

14 Claims, 2 Drawing Sheets

EXPANDABLE ANNULUS SEALING RING FOR STENTED MINIMALLY INVASIVE HEART VALVE PROSTHESES

CROSS-REFERENCE TO RELATED APPLICATIONS

This is the U.S. National Stage of International Application No. PCT/EP2015/071383 filed Sep. 17, 2015, which was published in English under PCT Article 21(2), and which in turn claims the benefit of European Patent Application No. 14185391.1 filed Sep. 18, 2014.

The invention relates to a medical implant according to claim 1.

Transcatheter heart valve implantations (THVI) represent an emerging field in clinical cardiovascular medicine as they provide the option to replace a diseased heart valve without an open heart surgical procedure.

All of today's commercially available THVI systems make use of bioprosthetic (biological) heart valves that are integrated into self-expandable or ballon-expandable stent systems. These stented valves are then "crimped" (i.e. reduced in radial diameter) and minimally invasively delivered into the orthotopic position of a native heart valve via a transfemoral or (at least) transapical catheter. This implies that these kinds of valves are used on the beating heart (off-pump) and do not require open heart surgery or the use of a heart lung machine, which makes them a highly attractive, novel approach for the treatment of valvular heart disease. The technology, which is currently primarily used for elderly patients, is expected to broaden its area of application to the broad population of patients with heart valve disease in general.

In spite of the principal clinical success of this technology, a major problem remains to be the paravalvular leakage reported for different types of transcatheter heart valve prostheses through the paravalvular annular area which is defined as the area between the medical implant (e.g. stent with bioprosthetic valve) and the vascular wall at the position of the native heart valve annulus (circular connective tissue). Paravalvular leakage results in chronic or—in severe cases—even in acute ventricular decompensation and therefore represents a major adverse event following transcatheter valve implantation.

Thus, the problem underlying the present invention is to provide for a medical implant that reduces the afore-mentioned leakage.

This problem is solved by a medical implant according to claim 1. Embodiments of the invention are stated in the sub claims and are explained below.

According to the invention, the first struts each comprise a recess, wherein the medical implant further comprises a sealing member arranged in said recesses, wherein said sealing member is formed annularly in said expanded state for sealing a leakage between the medical implant and a surrounding tissue (e.g. an annulus of a native heart valve). Particularly, the crimped state is a state, in which the structure comprises a smaller volume and/or radial diameter (e.g. perpendicular to the axis of the structure) than in the expanded state.

Due to arranging the sealing member in said recesses, the sealing member can be protected upon delivery be means of a catheter. Normally any such sealing member (also denoted as skirt) sutured to the outer surface of the medical implant has a high risk of becoming destroyed during the harmful delivery procedure where the implant is pushed out of an implantation sheath on the outer surface.

Further, according to an embodiment of the present invention, the sealing member is designed to expand from a first state into a second state for sealing a leakage between the scaffolding and said surrounding tissue, wherein in the second state the sealing member has a larger volume than in the first state.

Further, according to an embodiment of the present invention, the sealing member comprises a material that is fluid-sensitive so that the sealing member expands from the first state into the second state when the sealing member contacts a fluid, particularly blood. Such a material may comprise or may be formed as a non-woven fabric or a cellulosic absorbent (e.g. cotton or rayon) comprising a film or coating out of cellulose-hydrate (e.g. cellophane).

Further, according to an embodiment of the present invention, the sealing member comprises a material that is thermo-sensitive so that the sealing member expands from the first state into the second state when it reaches a pre-defined temperature, particularly 37° C. Such a material may comprise or may be formed as one of the following materials: a thermosensitive polymer, poly(N-isopropylacrylamide), hydroxypropylcellulose, poly(vinylcaprolactame).

Further, according to an embodiment of the present invention, each first strut comprises an outside facing outwards in the expanded state of the structure, wherein the respective recess is formed in said outside of the respective first strut. Particularly, in the expanded state, the respective outside faces away from an inner space of the structure that is defined or surrounded by the latter.

Further, according to an embodiment of the present invention, the sealing member is arranged in the respective recess in a form-fitting manner.

Further, according to an embodiment of the present invention, in its expanded second state the sealing member protrudes with a circumferential sealing portion which forms a surface for butting against said surrounding tissue out of the respective recess in a radial direction when the structure resides in its expanded state. The respective radial direction extends perpendicular to the axial direction of the expanded structure (starting from the axis of the structure).

Further, according to an embodiment of the present invention, the sealing member comprises a plurality of filling portions, wherein each filling portion is arranged in one of said recesses.

Particularly, in the second state of the sealing member, each filling portion protrudes out of its associated recess in a radial direction (see above) when the structure resides in its expanded state.

Particularly, in the first state of the sealing member one of the following holds for each filling portion:
- each filling portion does not protrude out of the associated recess in a direction normal to said outside of the respective strut,
- each filling portion is flush with the outside of the respective flush, or
- each filling portion protrudes out of its recess in a direction normal to said outside of the respective strut, wherein each filling portion protrudes further out of its recess in said direction normal to said outside of the respective strut in the second state of the sealing member.

Since a substantial part of the cross section of the sealing member (at the location of the respective recess) is actually arranged in the respective recess of the structure in the first state of the sealing member, namely particularly at least 50%, particularly at least 60%, particularly at least 70%, particularly at least 80%, particularly at least 90%, particularly at least 95%, particularly 100%, the sealing member has a good protection and is less likely to be ripped off upon delivery of the medical implant. Thus, the recesses serve as a protection for the sealing member, since they minimize the working surface (protruding portion) of the sealing member in the axial direction of the medical implant.

Further, according to an embodiment of the present invention each two neighboring filling portions are integrally connected via an intermediate portion that is arranged completely outside said recesses and extends from first strut to first strut.

Further, according to an embodiment of the present invention the structure defines/surrounds an inner space in the crimped and in the expanded state.

Further, according to an embodiment of the present invention, in the crimped state of the structure each intermediate portion of the sealing member is at least partially inserted into said inner space, particularly through an associated aperture delimited by two first struts (and particularly two second struts, see below) between which the respective intermediate portion extends. This also minimizes abrasive contact of the sealing member with other component during a transcatheter delivery.

Particularly, according to an embodiment of the present invention, the first struts each comprise two end regions. Particularly, each end region is connected, particularly integrally connected, to at least one second strut, particularly to two second struts.

Particularly, according to an embodiment of the present invention, said end regions of each first strut are integrally connected to each other via a central region, wherein the central region comprises the recess of the respective first strut, and wherein the central region is thicker (e.g. comprises a larger cross-sectional area and/or outer diameter) than the end regions connected to the respective central region. Particularly, the cross-sectional area and/or outer diameter increases continuously from either end region of a first strut towards the central region of the respective first strut. Particularly, due to the fact that the central region of the first strut is thicker, a sealing ring of sufficient size can be easily accommodated in the recesses and at the same time protected from abrasive impact.

Particularly, according to an embodiment of the present invention, the second struts are thinner than the central regions of the second struts and may comprise the cross-sectional area and/or outer diameter of the end regions of the first struts.

Further, according to an embodiment of the present invention, the structure may either be designed to be self-expandable or balloon-expandable.

Further, according to an embodiment of the present invention, particularly in case of a self-expandable structure, the latter particularly comprises or is built out of a superelastic metal alloy such as an alloy of Nickel and Titanium.

Particularly, said structure is made from an alloy comprising from about 50.5% (as used herein these percentages refer to atomic percentages) Ni to about 60% Ni, and most preferably about 55% Ni, with the remainder of the alloy Ti. Preferably, the structure is such that it is superelastic at body temperature, and particularly has an (Austenite finish temperature) Af in the range from about 24° C. to about 37° C. The superelastic design of the structure makes it crush recoverable which, as mentioned above, can be used for reducing the volume of the structure (and therefore of the implant) by crimping it, so as to deliver the implant by means of a catheter to an orthotopic position where it is to be expanded.

Alternatively, a balloon or another suitable means may be provided for expanding the structure and implant in situ mechanically.

Further, according to an embodiment of the present invention, the medical implant comprises a valve, particularly for replacing a deficient native heart valve, which valve is fastened to the structure and particularly arranged in the inner space of the structure in the expanded state of the structure, wherein particularly in the expanded state of the structure the heart valve is designed to allow flow of blood in a blood flow direction through the valve and two prevent back flow of blood in the opposite direction.

Particularly the valve is a bioprosthetic valve (i.e. a valve comprising biological tissue, e.g. from a porcine).

Particularly, the valve is designed as a pulmonary semilunar valve for passing blood from the right ventricle to the pulmonary arteries and for preventing back flow of blood from the pulmonary arteries into the right ventricle.

Further, particularly, the valve is designed as an aortic semilunar valve for passing blood from the left ventricle to the aorta and for preventing back flow of blood from the aorta into the left ventricle.

Further, particularly, the valve is designed as a mitral valve for passing blood from the left atrium to the left ventricle and for preventing back flow of blood from the left ventricle into the left atrium.

Further, particularly, the valve is designed as a tricuspid valve for passing blood from the right atrium into the right ventricle and for preventing back flow of blood from the right ventricle into the right atrium.

Further, according to an embodiment of the present invention, the sealing member, particularly said surface of the circumferential sealing portion, is designed to contact the anatomical annulus of a native valve when the structure is positioned in situ and expanded into its expanded state, particularly such that the sealing member prevents a paravalvular leakage between the annulus and the medical implant.

Further, according to an embodiment of the present invention, the medical implant is designed to be brought into an orthotopic position of a native human heart valve via a catheter device (e.g. the medical implant is a transcatheter medical implant), particularly in a way as described above, so that the sealing member, particularly said surface of the circumferential sealing portion, contacts the anatomical annulus of a native valve when the structure is positioned in situ and expanded into its expanded state.

According to a further aspect of the present invention, a medical implant system is disclosed, comprising a medical implant according to the invention and a catheter device for delivering the medical implant into an orthotopic position of a native human heart valve, particularly in a way as described above, so that the sealing member, particularly said surface of the circumferential sealing portion, contacts the anatomical annulus of a native valve when the structure is positioned in situ and expanded into its expanded state.

In the following, further features and embodiments of the present invention shall be described with reference to the Figures, wherein FIG. 1 shows a view of an implant device according to the invention for replacing a deficient native heart valve of a human being;

Figure 1:
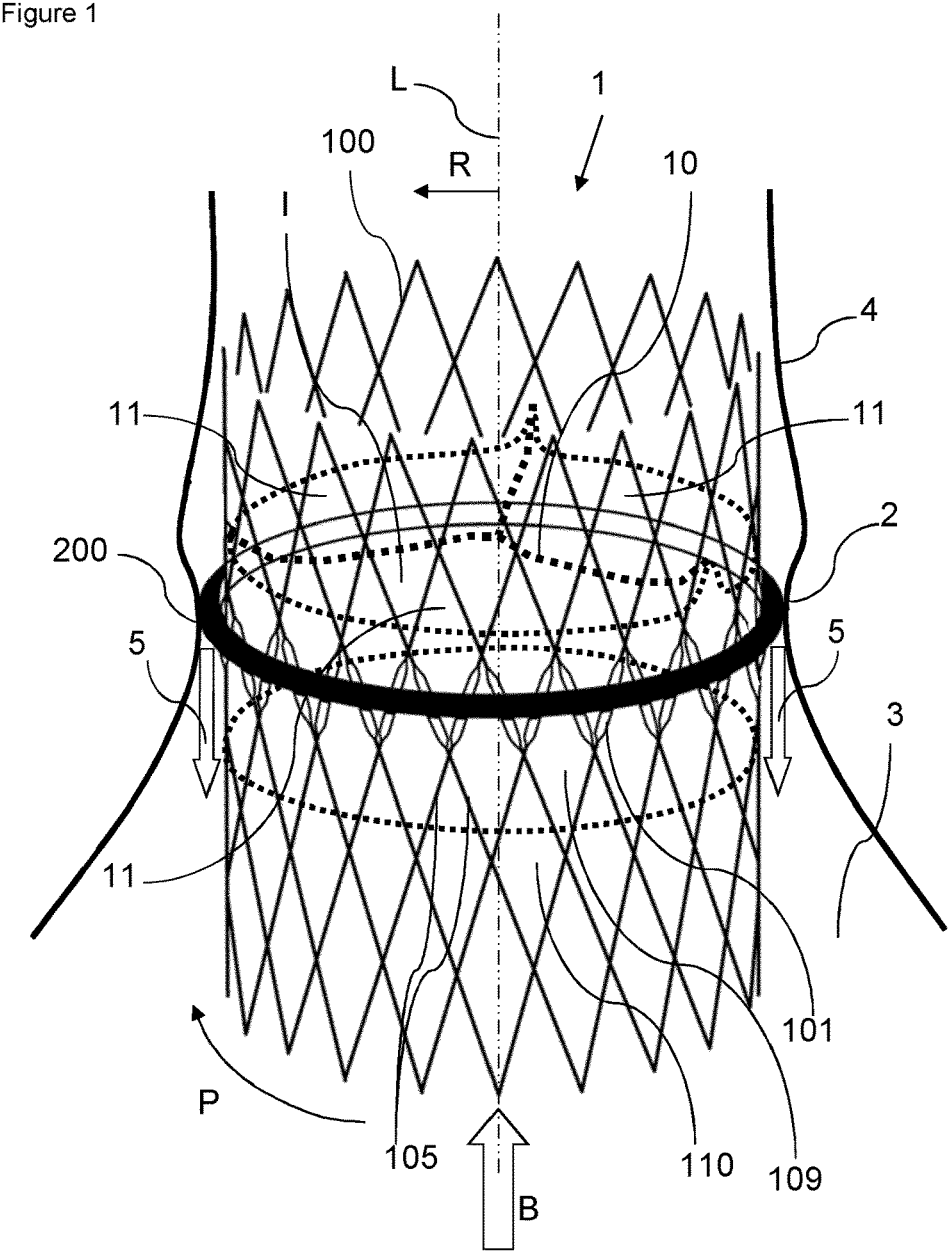

Previous stent systems exhibit a paravalvular leakage as indicated in FIG. 1 by arrows 5 due to which blood leaks through between the vascular wall 2 and the implant 1. To reduce the risk of such a paravalvular leakage, the present invention relates to a medical implant 1 that comprises a structure 100 (shortly also denoted as "stent") that is composed of locally thicker first struts 101 at the position of the valvular annulus 2. Integrated into these thickened central regions 104 of first struts 101 are recesses O within the first struts 101 forming a small, well defined channel at the outer surface of the structure 100. The recesses O represent zones with reduced thickness of the first struts 101. The created channels serve as place holders for the integration of a sealing member (e.g. O-ring) 200 also denoted as skirt that is protected by the surrounding thicker areas of the central regions 104 of the first struts 101 (cf. FIGS. 3 and 4). The integrated sealing member 200 is particularly made out of a thermo-sensitive and/or fluid-sensitive material that—following blood contact or temperatures of 37 degree Celsius—will respond with significant volume extension/swelling. The swelling will be homogeneously distributed over the entire circular area of the sealing member 200. As a result, the swollen sealing member 200 will tighten the annular region between the implant 1 and the surrounding tissue 2 and will therefore serve as a sealing ring in the orthotopic (annular) position in situ. The sealing member 200 can be manufactured out of different temperature- and/or fluid-sensitive materials. This construction will help to significantly reduce the para-implant blood leakage after minimally invasive heart valve implantation.

Figure 2:
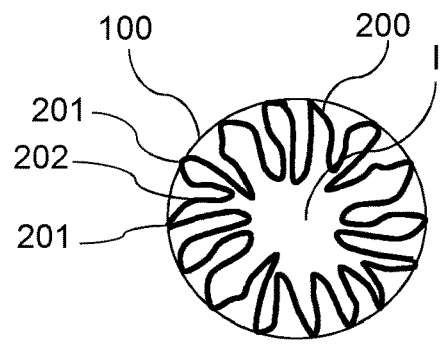
FIG. 2 shows a schematical top view of the implant in a crimped state.
Figure 3:
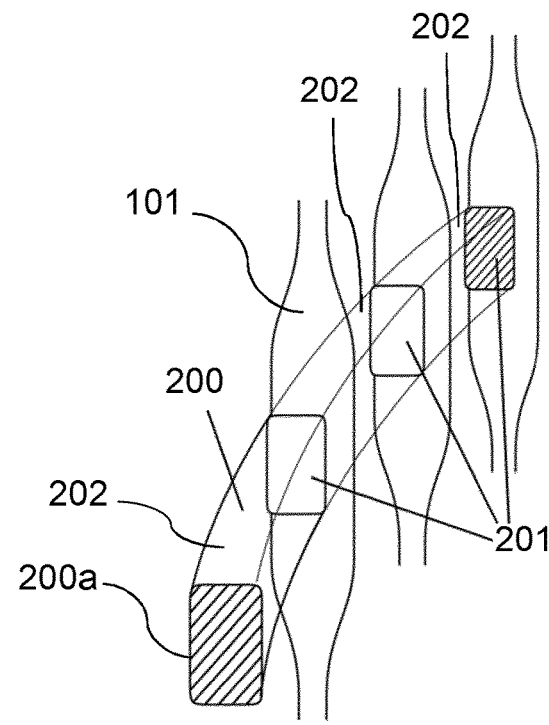
FIG. 3 shows a detail relating to first struts of the structure of implant device.
Figure 4:
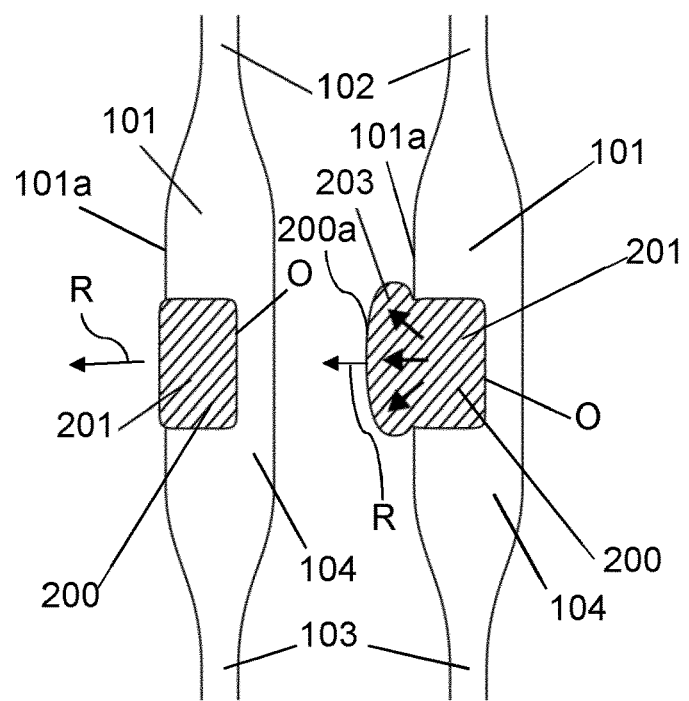
FIG. 4 shows a sealing member of the implant in a first and in an expanded second state.

In detail, as shown in FIG. 1 in conjunction with FIGS. 2 to 4, the medical implant 1 according to the invention comprises an expandable structure 100 (also denoted as stent) which is designed to be expanded from a crimped state (indicated in FIG. 2 showing a schematical top view of the implant 1) into an expanded state, in which the structure 100 forms a tubular scaffolding as shown in FIG. 1.

The structure 100 holds a valve 10 which may comprise a plurality of leaflets 11 (e.g. three leaflets 11) and serves for replacing a deficient native heart valve. The valve 10 is arranged in the inner space I of the structure 100 and is designed to allow flow of blood in a blood flow direction B along the axis L of the structure 100 through the valve 10 and two prevent back flow of blood in the opposite direction. Particularly, the valve 10 is a bioprosthetic valve (i.e. a valve comprising biological tissue, e.g. from a porcine). Here, the valve 10 is designed as a (e.g. semilunar) valve for passing blood from the left ventricle 3 to the left pulmonary artery 4 and for preventing back flow of blood from the left pulmonary artery 4 into the left ventricle 3.

When the structure 100/implant 1 is located in the orthotopic position of the deficient heart valve it is expanded and pushes away the deficient valve that is to be replaced by valve 10. The sealing member 200 then contacts the anatomical annulus 2 of the deficient native valve so that a paravalvular leakage between the annulus 2 and the medical implant 1 is prevented.

For receiving the sealing member 200, the structure 100 comprises a plurality of first struts 101 arranged along a peripheral direction P of the structure 100 in its expanded state.

The first struts 101 each comprise two end regions 102, 103 (cf. FIG. 4) wherein each end region 102, 103 is connected, particularly integrally, to a further first strut 101 as well as to two second struts 105. In this way, in the expanded state of the structure 100, (each) two neighbouring first struts 101 form a diamond-shaped (rhombic) cell 109 with two second struts 105. Further, the remaining part of structure 100 comprises diamond-shaped cells 110 which are merely generated by four second struts 105, respectively.

The end regions 102, 103 of each first strut 101 are integrally connected to each other via a central region 104 of the respective first strut 101, wherein the central regions 104 of the first struts 101 each comprise one of said recesses O on an outside 101a of the respective first strut 101 for receiving the sealing member 200. As shown for instance in FIG. 4, the central region 104 of each first strut 101 is thicker (e.g. comprises a larger cross-sectional area and/or outer diameter) than the end regions 102, 103 of the respective first strut 101. Particularly, the cross-sectional area and/or outer diameter increases continuously from either end region 102, 103 of a first strut 101 towards the central region 104 of the respective first strut 101. In this way, the first struts 101 can hold the sealing member 200 while protecting it at the same time from abrasive impact. As shown in FIG. 1, the second struts 105 are thinner than the central regions 104 of the first struts 101 and comprise the cross-sectional area and/or outer diameter of the end regions 102, 103 of the first struts 101.

Furthermore, the first struts 101 are connected to each other via their end regions 102, 103 such that the first struts 101 extend along a zig-zag course as shown in FIG. 1. Therefore, in the expanded state of the structure 100, the recesses O are arranged along the peripheral direction P of the structure 100 so that the sealing member 200 arranged in said recesses O in a form-fitting manner forms an annular sealing member 200 (so called O-ring) in the expanded state of the structure 100.

As already described above, the sealing member 200 is designed such that it will increase its volume significantly once exposed to a fluid like e.g. blood and/or the body temperature of 37°. This is shown on the right hand side of FIG. 4. In this configuration, which is denoted as second (expanded) state of the sealing member 200, the latter protrudes out of its recesses O with a circumferential sealing portion 203 in the radial direction R (i.e. normal to said outsides 101a of the first struts 101), so that the entire sealing member or ring 200 now protrudes from the outside of the structure 100 and butts with a surface 200a of the sealing member 200 against the annulus 2 in order to prevent the paravalvular leakage 5. In contrast, before expansion, as shown on the left hand side of FIG. 4, the sealing member 200 when residing in its first state is essentially arranged flush with the outside 101a of the respective first strut 101 and thus protected against abrasive impact.

For delivery of the implant, intermediate portions 202 of the sealing member 200 which connect filling portions 201 of the sealing member 200 that are actually integrated into the recesses O are folded through the openings provided by the cells 109, 110 into an inner space of the implant 1 as shown in FIG. 2. This allows to minimize contact between the sealing member 200 and a surrounding catheter part during delivery of the medical implant 1 to the position of the native heart.

The invention claimed is:
1. A medical implant, comprising:
an expandable structure (100) which is designed to be expanded from a crimped state into an expanded state, wherein the structure (100) forms a tubular scaffolding in the expanded state, and wherein the structure (100)

comprises a plurality of first struts (101) arranged along a periphery of the structure (100) in said expanded state, characterized in that, the first struts (101) each comprise a recess (O), wherein the medical implant (1) further comprises a sealing member (200) arranged in said recesses (O), wherein said sealing member (200) is formed annularly in said expanded state, wherein each first strut (101) comprises an outside (101a) facing outwards in the expanded state of the structure (100), wherein the respective recess (O) is formed in said outside (101a) of the respective first strut (101) in a thickened region (105) of the respective first strut (101).

2. The medical implant according to claim 1, characterized in that the sealing member (200) is designed to expand from a first state into a second state, wherein in the second state the sealing member (200) has a larger volume than in the first state.

3. The medical implant according to claim 2, characterized in that the sealing member (200) comprises a material that is fluid-sensitive so that the sealing member (200) expands from the first state into the second state when the sealing member (200) contacts a fluid, particularly blood.

4. The medical implant according to claim 2, characterized in that the sealing member (200) comprises a material that is thermo-sensitive so that the sealing member (200) expands from the first state into the second state when it acquires a pre-defined temperature, particularly 37° C.

5. The medical implant according to claim 1, characterized in that the sealing member (200) is arranged in the respective recess (O) in a form-fitting manner.

6. The medical implant according to claim 2, characterized in that in its expanded second state the sealing member (200) protrudes with a circumferential sealing portion (203) which forms a surface (200a) for butting against said surrounding tissue (2) out of the respective recess (O) in a radial direction (R) when the structure (100) resides in its expanded state.

7. The medical implant according to claim 1, characterized in that the sealing member (200) comprises a plurality of filling portions (201), wherein each filling portion (201) is arranged in one of said recesses (O).

8. The medical implant according to claim 7, characterized in that each two neighbouring filling portions (201) are integrally connected via an intermediate portion (202) that is arranged outside said recesses (O).

9. The medical implant according to claim 8, characterized in that the structure (100) defines an inner space (I) in the crimped and in the expanded state.

10. The medical implant according to claim 9, characterized in that in the crimped state of the structure (100) each intermediate portion (202) is at least partially inserted into said inner space (I).

11. The medical implant according claim 1, characterized in that the structure (100) is self-expandable from the crimped state into the expanded state or balloon-expandable.

12. The medical implant according to claim 1, characterized in that the medical implant (1) comprises a valve (10), particularly for replacing a deficient native heart valve, which valve (10) of the medical implant (1) is fastened to the structure (100).

13. The medical implant according to claim 1, characterized in that the sealing member (200) is designed to contact the anatomical annulus (2) of a native valve when the structure (100) is expanded into its expanded state, particularly such that the sealing member (200) prevents a paravalvular leakage between the annulus and the medical implant (1).

14. The medical implant according to claim 1, characterized in that the medical implant (1) is designed to be brought into a orthotopic position of a native heart valve via a catheter device.

\* \* \* \* \*